United States Patent [19]

Inahara

[11] Patent Number: 5,036,869

[45] Date of Patent: Aug. 6, 1991

[54] MEDICAL WIRELESS TELEMETER

[75] Inventor: Kazuo Inahara, Kawagoe, Japan

[73] Assignee: Nihon Kohden Corporation, Tokyo, Japan

[21] Appl. No.: 498,812

[22] Filed: Mar. 23, 1990

[30] Foreign Application Priority Data

Mar. 30, 1989 [JP] Japan .................... 1-36816[U]

[51] Int. Cl.$^5$ ........................................ A61B 5/04
[52] U.S. Cl. ................................. 128/903; 128/696
[58] Field of Search ............... 128/696, 695, 903, 904, 128/668

[56] References Cited

U.S. PATENT DOCUMENTS

| 3,253,588 | 5/1966 | Vuilleumier et al. | 128/903 |
| 3,695,253 | 10/1972 | Vielhauer | 128/695 |
| 3,972,320 | 8/1976 | Kalman | 128/903 |
| 4,319,241 | 3/1982 | Mount | 128/904 |
| 4,675,656 | 6/1987 | Narcisse | 128/903 |
| 4,827,943 | 5/1989 | Bornn et al. | 128/668 |
| 4,889,131 | 12/1989 | Salem et al. | 128/903 |
| 4,981,141 | 1/1991 | Segalowitz | 128/903 |

Primary Examiner—Francis Jaworski
Assistant Examiner—George Manuel
Attorney, Agent, or Firm—Hoffmann & Baron

[57] ABSTRACT

A medical wireless telemeter includes a transmitter section having one or more different types of transmitters corresponding to different medical body signals to be transmitted as a telegram to a receiver. The receiver has different body signal processing circuits corresponding to the various types of number of medical body signals which may be sent by the transmitter. A process or specifying circuit specifies a particular body signal processing circuit after the receiver identifies the particular transmitter kind code from the telegram received after the transmitter identification code has been received which specifies the particular medical body measurement analysis to be conducted.

2 Claims, 4 Drawing Sheets

FIG. 2a
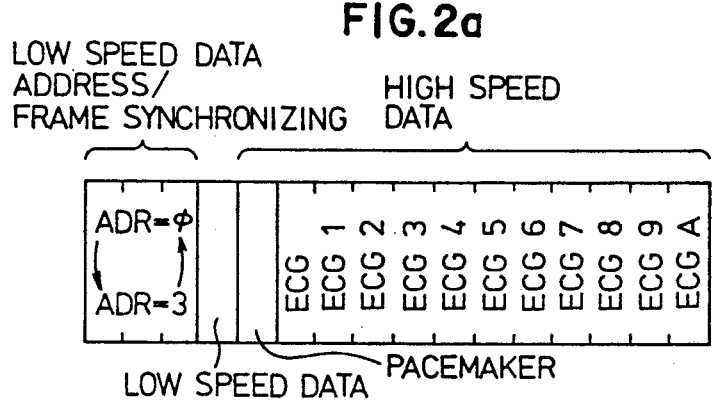
FIG. 2b
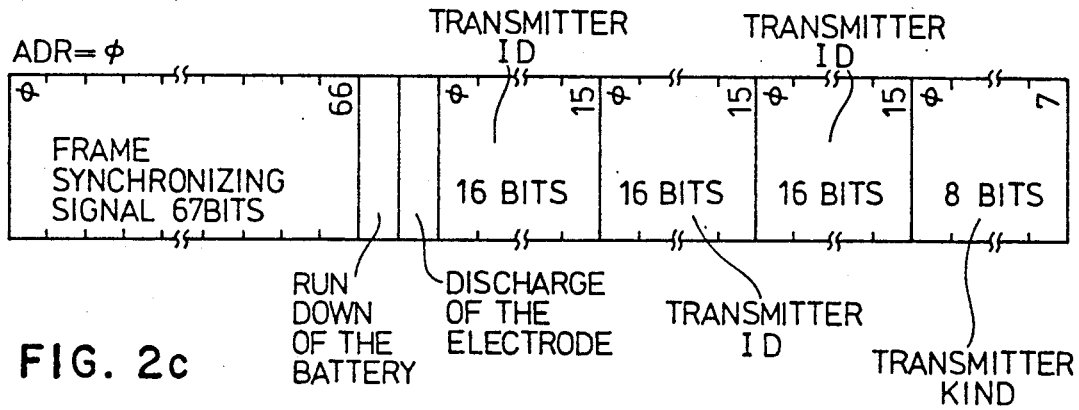
FIG. 2c
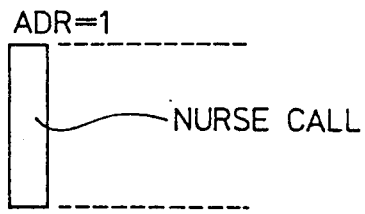
FIG. 2d
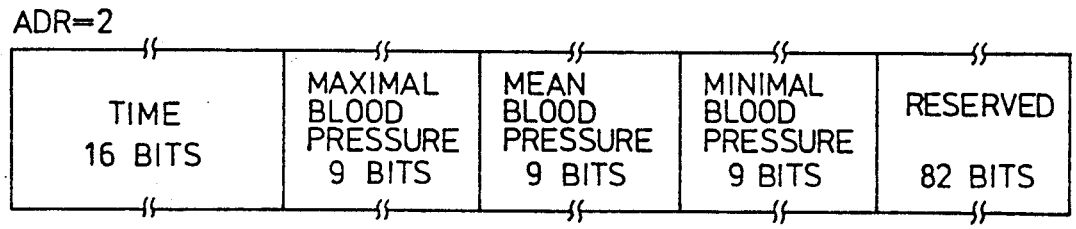
FIG. 2e
ADR=3
RESERVED DATA

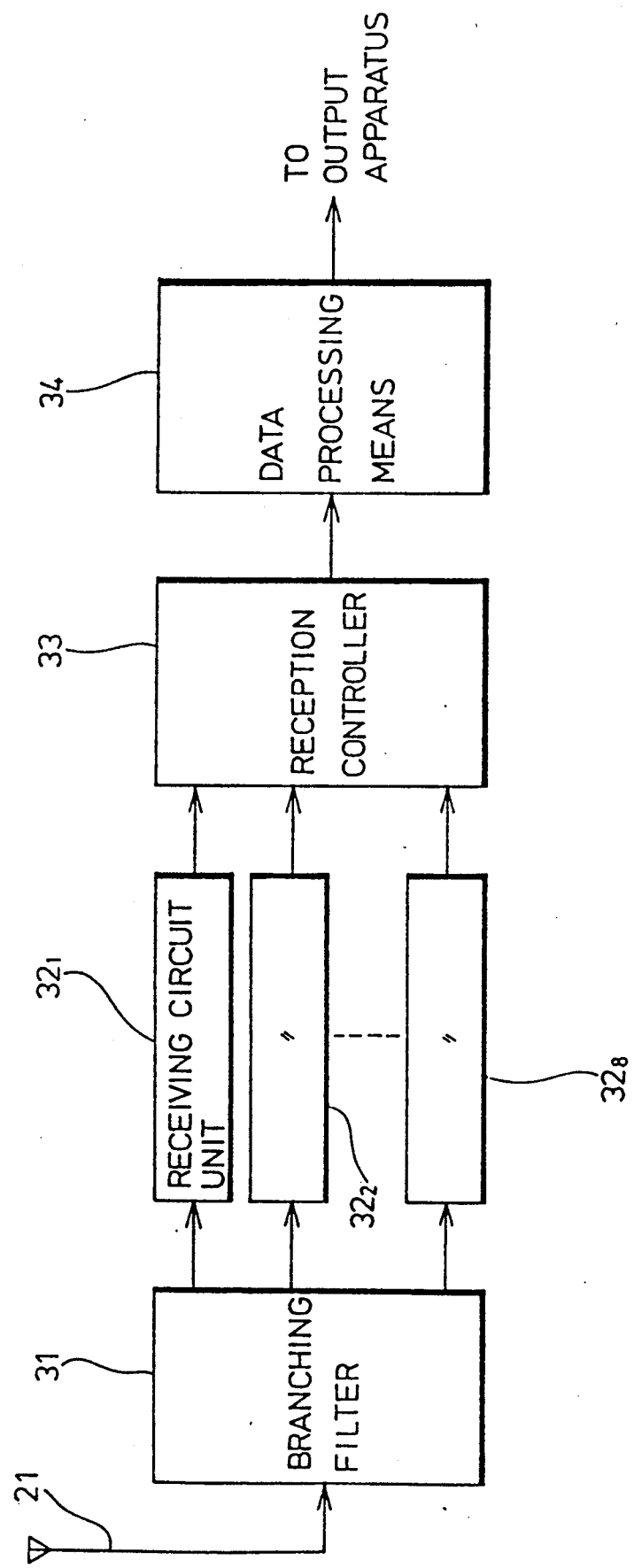

5,036,869

MEDICAL WIRELESS TELEMETER

BACKGROUND OF THE INVENTION

1. Field of the Invention

The present invention relates to a wireless medical telemeter having a transmitter that transmits a medical body signal from a human body as a telegram encoded with a synchronizing signal and with a plurality of bits, and a receiver which receives the transmitted medical telegram, processes and decodes the transmitted data, and then displays or prints out medical information corresponding to the transmitted data.

2. Description Of The Related Art

The transmitter and the receiver of a conventional medical wireless telemeter system are usually constructed and used as a pair. When the condition of the patient changes and additional or different medical information is required, both the transmitter and receiver should be replaced.

In order to give the telemeter system adequate flexibility, the range of the occupied band may be extended, this extended range corresponding to any increase in the number or type of medical measuring items used. However, the increase in bandwidth causes a decrease in the S/N ratio. It should also be noted that the spectral band occupied by the medical wireless telemeter is reserved by law.

OBJECTS AND SUMMARY OF THE INVENTION

It is the primary object of the present invention to provide a medical wireless telemeter which can transmit many different measured readings of the human body within a narrow occupied band.

To accomplish this object, the transmitter section of the telemeter is constructed from at least one selected transmitter of different kinds of transmitters, the transmitter section transmitting a telegram composed of one or more different kinds of transmitter signals according to the specific body signal to be transmitted. The receiver section of the telemeter is constructed with a plurality of different kinds of body signal processing means, which performs data processing corresponding to the plurality of kinds of signals which may be received, and data-processing specifying means which specifies the type of body signal processing means adapted to process a respective body signal received after identifying the transmitter kind code from the telegram.

After receiving the transmitting signal transmitted by each transmitter used, the receiver identifies the transmitter code of each transmitter, specifies which data processing is to be performed, and performs the specific data-processing required of that respective body signal. The results of the data-processing is provided to an output system for monitoring.

Thus, various types of medical body signals may be monitored by substituting various transmitters while using the same receiver and operating within a relatively narrow band.

These and other objects, features and advantages of this invention will be apparent from the following detailed description of illustrative embodiments thereof, which is to be read in connection with the accompanying drawings.

BRIEF DESCRIPTION OF THE DRAWINGS

FIGS. 2a, 2b, 2c, 2d and 2e; illustrates the format of the telemeter signal transmitted by transmitter section;

FIG. 5 is a block diagram of the receiver of the telemeter of the present invention formed in accordance with another embodiment.

DESCRIPTION OF THE PREFERRED EMBODIMENTS

A medical wireless telemeter according to one embodiment of the present invention will now be described.

Figure 1:
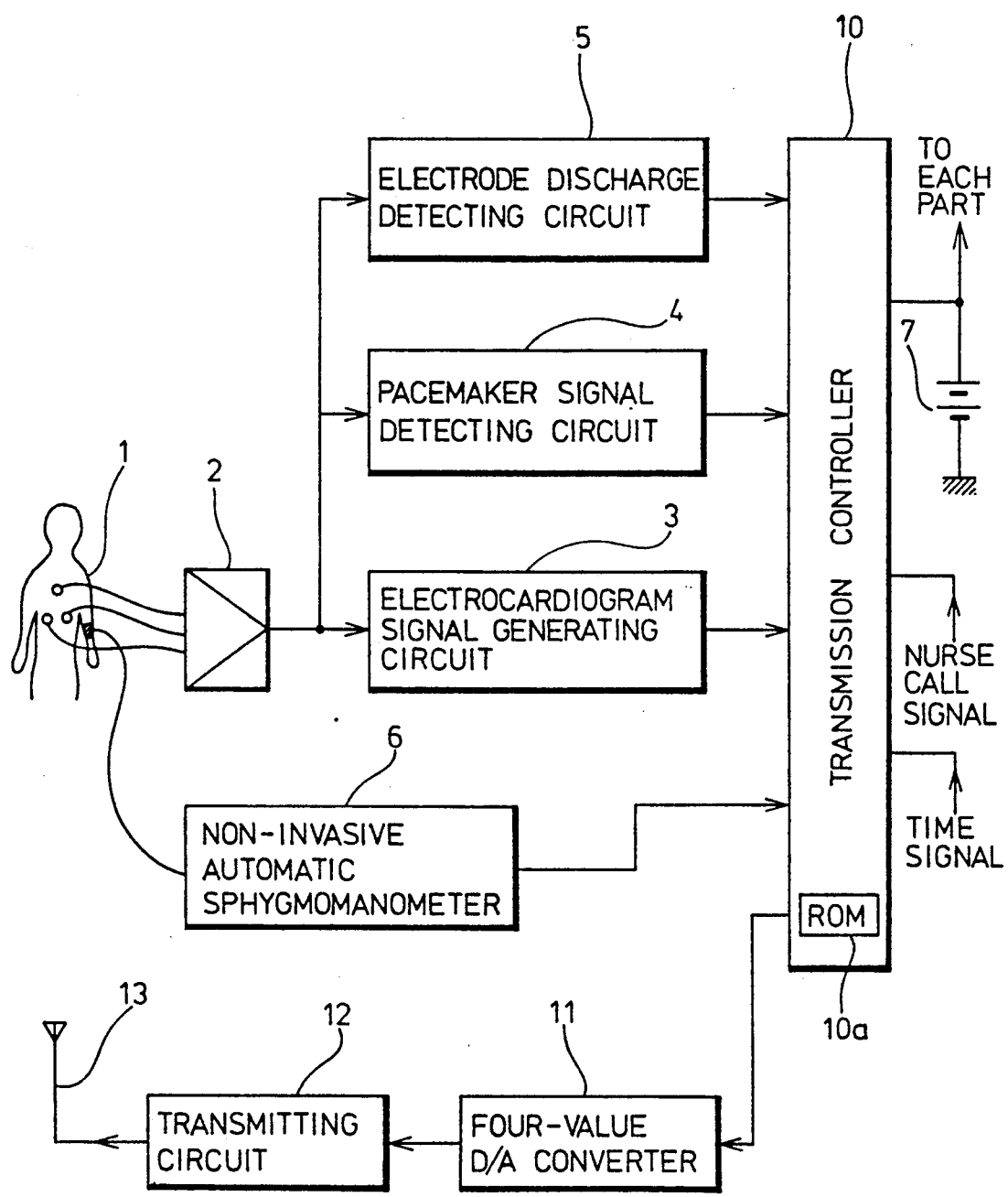
FIG. 1 is a block diagram of the transmitter section of the telemeter formed in accordance with the present invention.

FIG. 1 illustrates the transmitter section of the telemeter, including a transmitter for an electrocardiogram, which is one specific type of transmitter of a plurality of different types of transmitters which may be selected for use to communicate with the same receiver.

In this figure, an amplifier 2 amplifies the electrocardiogram reading of a body 1 detected by an electrode. Then, an electrocardiogram signal generating circuit 3 outputs a digital electrocardiogram signal after sampling and A/D converting the output from amplifier 2. A pacemaker signal detecting circuit 4 detects a pacemaker signal in the amplified output. An electrode discharge detecting circuit 5 similarly monitors the amplified output and detects a discharge from the electrode, the term "discharge" meaning that the electrode becomes detached or separated from the body. A non-invasive automatic sphygmomanometer 6 periodically outputs the readings of maximal, mean and minimal blood pressure.

A transmission controller 10 having a central processing unit ("CPU") inputs the aforementioned pacemaker signal, the blood pressure signal bearing the electrocardiogram and time signal, the voltage of an electric battery 7 in order to monitor the remaining energy of the battery, and a nurse call signal indicating whether the nurse has been called. The transmission controller 10 next prepares the telegrams, whose formats are shown in FIG. 2, as time-shared signals comprising 16 bits a frame by 4 ms. As shown in FIG. 2 (a), the transmission controller 10 prepares low speed data address signals in addition to frame synchronizing signals circulating 000→001→010→011→000 with the first three bits. The controller 10 inputs the low speed address signal described below at the fourth bit, sends the presence or the absence of the pacemaker signal at the fifth bit and prepares the sampling data of the electrocardiogram signal with the remaining eleven bits. As shown in FIGS. 2 (b) to (e), the low speed data specified by a low speed address ADR prepare the three kinds of low speed data of 125 bits.

As shown in FIG. 2 (b), the transmission controller 10 prepares a frame synchronizing signal with the first 67 bits at ADR=0, sequentially allots a run down battery signal and a discharged electrode signal with the next two bits, continuously allots three times the transmitter ID code signal of 16 bits stored in a ROM 10a after reading out and allots the remaining 8 bits to the transmitter kind signal. In this embodiment, the electrocardiogram signal which is stored in the ROM 10a is transmitted with the last 8 bits. As shown in FIG. 2 (c), a nurse call signal is allotted to the first one bit at ADR=1. As shown in FIG. 2 (d), the transmission controller allots a time signal at the time of measuring blood pressure to the first 16 bits, prepares the maximal, mean and minimal blood pressure signal as 9 bits and reserves the remaining 82 bits at ADR=2. Similarly, ADR=3 is reserved.

A four-value D/A converter 11 converts the telegrams prepared as described above into four values of analogue signals in order to transmit them by two bits. A transmitting circuit 12 transmits this four-value signal from an antenna 13 after FM-modulating.

Figure 3:
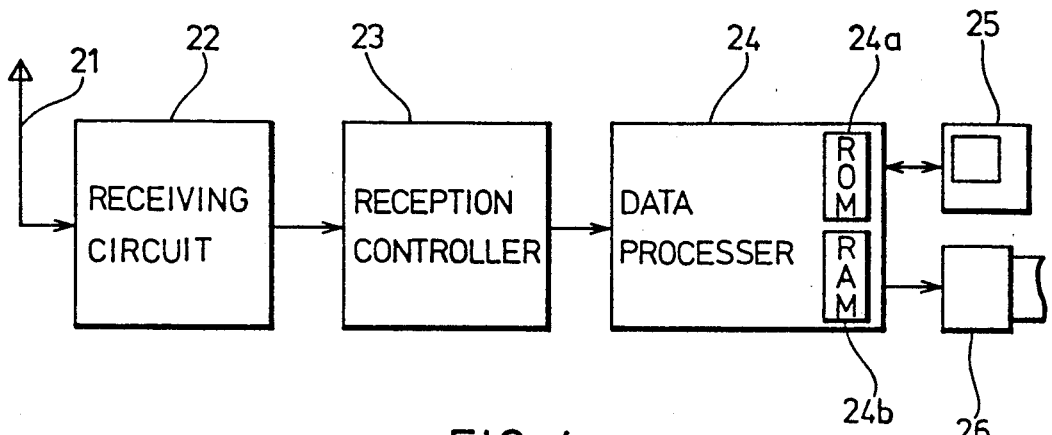
FIG. 3 is a block diagram of a receiver of the telemeter formed in accordance with the present invention.

FIG. 3 is a block diagram of a receiver circuit which communicates with each transmitter of the telemeter system transmitter. In this figure, the telemeter transmission signal is received by an antenna 21. Then a receiving circuit 22 FM—demodulates the signal before sequentially outputting the decoded four-value signal transmission which is then A/D—converted to the 2 bit signal synchronized with the regenerating clock.

A reception controller 23 having a CPU regenerates the telemeter transmission data shown in FIG. 2. This is accomplished by retrieving the frame synchronization in the decoded transmission output from the receiving circuit 22 and converting the various transmitted signals into parallel data of 16 bits.

A data processor 24 which has a CPU that cooperates with a ROM 24a and a RAM 24b inputs the regenerated signal supplied from the reception controller 23. The data processor 24 then displays or prints the body measuring data using a cathode ray tube displaying apparatus 25 and a recorder 26 with a specified format in a monitor mode. The output is composed of medical data from body signals which are data-processed according to the transmitter kind code, the nurse call signal, and the battery-low signal. The data processor 24 also registers the transmitted patient ID code as the reference ID code in a transmitter register mode.

Figure 4:
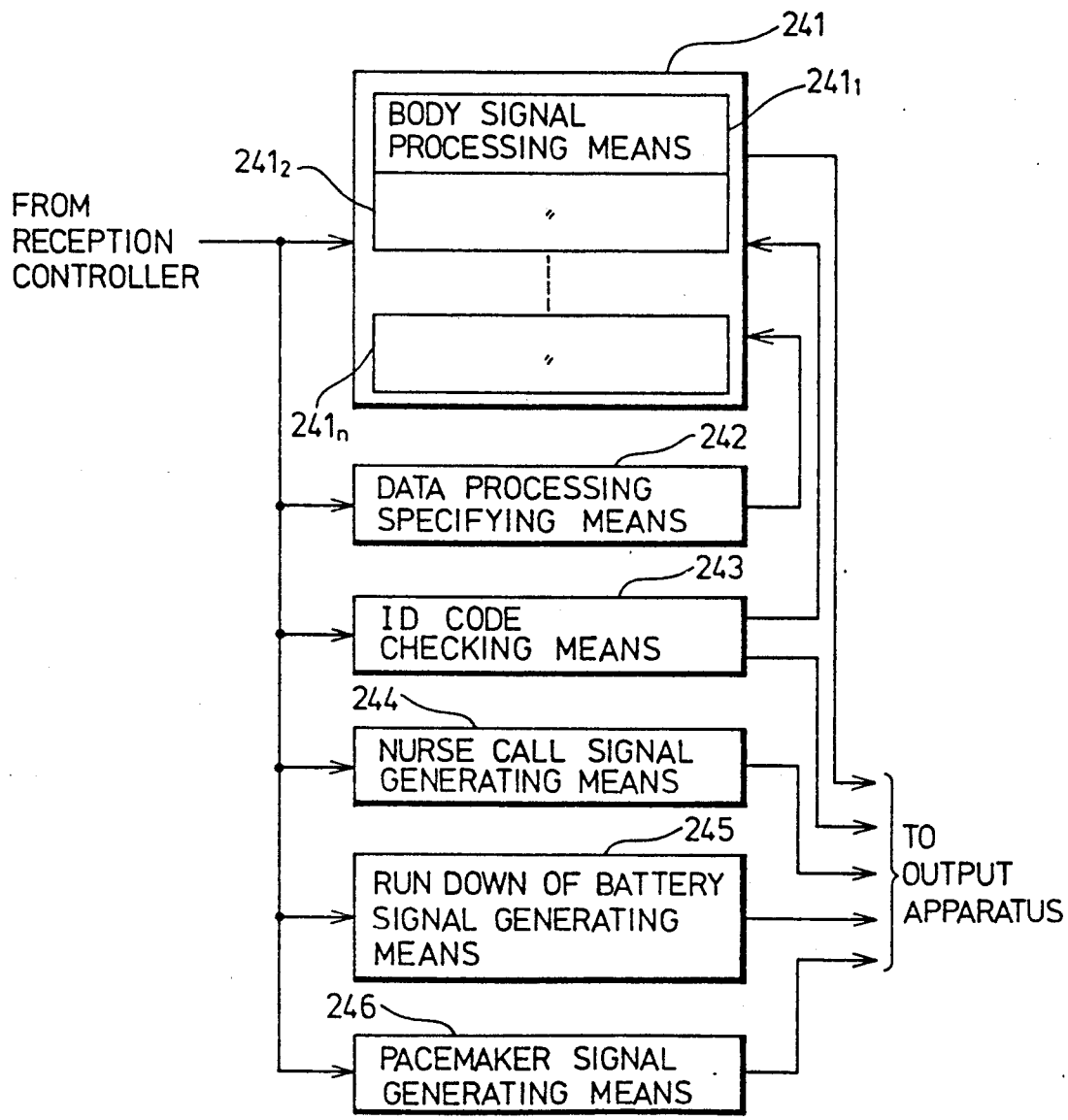
FIG. 4 is a more detailed block diagram of a portion of the receiver shown in FIG. 3.

FIG. 4 is a functional block diagram of the operation of the data-processing part 24 obtained by the operation of the CPU according to the program.

The data-processing part 24 is constructed to have N number of body signal processors ($241_1$ to $241_n$) available to process the data corresponding to the kind of body signal received and according to the plurality of kinds (n) of programs stored in the ROM 24a. The data processor 24 also has a data-processing specifying means 242 which identifies the corresponding body signal processor ($241_1$ to $241_n$) to be used after storing the transmitter kind code in the RAM 24b. An ID code checking means 243 registers the transmitted ID code to the RAM 24b as a reference code and continues the regular processing operation while the ID code is transmitted and until the transmitted ID code is not in accord with the reference code. A nurse call signal generating means 244 causes the display apparatuses 25 and 26 to display a nurse call indication when the nurse call signal is detected. A battery low generating means 245 causes the display apparatuses 25 and 26 to display a low battery indication when the battery-low signal is detected. For example, to process the electrocardiogram signal as shown in FIG. 1, the data processing part 24 prepares the trend data of maximal, minimal and mean blood pressures at specified intervals by preparing the trend data of the heart rate, detecting an arrhythmia and recording the time.

The operation of a telemeter thus constructed is as follows:

When the transmitter for the electrocardiogram shown in FIG. 1 is used, the receiver shown in FIG. 3 is turned to the transmitter register mode and the transmitter is operated. The telemeter receiver stores the received and decoded ID codes as the reference ID codes. The receiver stores the transmitter kind code simultaneously as the reference transmitter kind code. The receiver then specifies the program for electrocardiogram signal processing and terminates the transmitter register mode.

The ID codes are then compared with the reference ID codes one by one in the monitor mode, and the received transmission is judged as not regular when it is not coincident with the reference code. The telemeter signal shown in FIG. 2 is transmitted from the transmitter at every frame if it is the high speed data, and is sequentially transmitted at every bit from the transmitter for every frame in the 125 bits of low speed data of the address which is sequentially specified at every frame if it is the low speed data. This transmitted signal is received by the receiving circuit 22 in the receiver through the antenna 21, is decoded as a time-shared serial data of 16 bits and is supplied to the reception controller 23. After this, the data-processing means 24 causes the cathode ray displaying apparatus 25 and the recorder 26 to display the heart rate trend, the detected result of the arrhythmia, the trend data of the maximal, minimal and mean blood pressure and the time each was recorded, and the pacemaker signal. The data-processing means also causes the cathode ray tube displaying apparatus 25 to provide a nurse call or battery-low indication when applicable.

When the transmitter is changed to a different type according to the condition of the patient, the reference ID code and the reference transmitter kind signal are reset in the transmitter register mode. Although a group of the transmitters can be set at the same transmission cycle according to the present invention, they can be constructed so that the receiving cycle of the receiver can be adjusted if the transmission cycles differ. Then, the required data-processing is performed after the transmitter sends the data and the corresponding processing program is selected in the receiver.

FIG. 5 shows another embodiment of the multi-channel telemeter of the present invention. Eight receiving circuit units ($32_1$ to $32_8$), which correspond to transmitting frequencies are freely connected or disconnected to the receiver so as to be connected to a branching filter 31 succeeding to an antenna 21. The reception controller 33 receives the output signals of the receiving circuit units and parallel processes the signals. The output signals of the reception controller 33 are provided to the data-processing means 34 which performs the processing of the medical body signals in parallel and in accordance with the programs specified by the transmitter kind codes identified from the received signals. The body signals are then displayed by the output apparatus as a multi-channel display. With this embodiment, the medical body signals of different types of transmitters may be simultaneously monitored.

Although illustrative embodiments of the present invention have been described herein with reference to the accompanying drawings, it is to be understood that the invention is not limited to those precise embodiments and that various other changes and modifications may be effected therein by one skilled in the art without departing from the scope or spirit of the invention.

What is claimed is:

1. A medical wireless telemeter, which comprises:
a time-share transmitter means for transmitting a medical body measurement signal encoded as a telegram having a plurality of bits and a synchronizing signal, the time-share transmitter means compressing at least one selected transmitter of a plurality of different kinds of transmitters, each transmitter of the plurality of different kinds of transmitters being adapted to send a different medical body measurement signal using the same transmitting frequency, the at least one selected transmitter, means selected according to the kind of medical data to be transmitted, the time-share transmitter, means further comprising means for transmitting the telegram by a transmitter identifying the at least one selected transmitting means used in the time-share transmitter means;
a receiver means for receiving and decoding said medical body measurement signal and providing data-processed medial body measuring data corresponding thereto, the receiver means comprising a plurality of body signal and data-processing means, each body signal and data-processing means corresponding to at least one of the plurality of different kinds of transmitters and being adapted to data-process any one of the plurality of different medical body measurement signals, the receiver means further comprising transmitter kind code identifying means, the transmitter kind code identifying means adapted to receive the transmitter kind code transmitted from the time-share transmitter means and identifying the at least one selected transmitter means from the code used in the time-share transmitter means, the transmitter kind code identifying means adapted to provide a transmitter identifying signal, the receiver means further comprising data-processing specifying means, the data-processing specifying means being responsive to the transmitter identifying signal and adapted to select one of the plurality of body signal and data-processing means corresponding to the at least one selected transmitted means of the time-share transmitter means of the medical wireless signal transmitted by the at least one selected transmitter means; and
the receiver means outputting the data-processed medical body measuring data corresponding to the medical body measurement signal to a display apparatus.

2. A medical wireless telemeter comprising:
a transmitter means for time-share transmitting a medical body measurement signal and a synchronizing signal as a telegram encoded with a plurality of bits, said transmitter means comprising a plurality of different kinds of transmitters, each of said transmitters being adapted to send a different medical body measurement signal and transmitting a telegram including a transmitter kind code signal different from each other, said transmitter kind code signal corresponding to a respective one of said plurality of different kinds of transmitters;
a receiver means for receiving, decoding and data-processing said telegram to produce medical body measurement data, said receiver means outputting said medical body measurement data to an input apparatus, said receiver means comprising a plurality of body signal processing means each of the plurality of body signal processing means corresponding to a respective one of said plurality of different kinds of transmitters, said receiver means comprising a data-processing specifying means for identifying said transmitter kind code signal of said telegram and specifying one of said plurality of body signal processing means.

* * * * *